United States Patent [19]

Schröder et al.

[11] Patent Number: 4,944,791
[45] Date of Patent: Jul. 31, 1990

[54] HERBICIDAL HYDANTOINS

[75] Inventors: Ludwig Schröder, Ingelheim; Werner Stransky, Gau-Algesheim; Rudolf Mengel, Ingelheim, all of Fed. Rep. of Germany; Erich Raddatz, Cali, Colombia; Sigmund Lust, Darmstadt; Gerbert Linden, Ingelheim; Gerhart Schneider, Mühltal, all of Fed. Rep. of Germany

[73] Assignee: Shell Internationale Research Maatschappij B.V., The Hague, Netherlands

[21] Appl. No.: 284,093

[22] Filed: Dec. 14, 1988

Related U.S. Application Data

[63] Continuation of Ser. No. 157,903, Feb. 17, 1988, abandoned, which is a continuation of Ser. No. 46,622, May 4, 1987, abandoned, which is a continuation of Ser. No. 856,825, Apr. 18, 1986, abandoned, which is a continuation of Ser. No. 774,901, Sep. 11, 1985, abandoned, which is a continuation of Ser. No. 623,961, Jun. 25, 1984, abandoned, which is a continuation of Ser. No. 492,946, May 9, 1983, abandoned, which is a continuation-in-part of Ser. No. 479,709, Mar. 28, 1983, abandoned.

[30]         Foreign Application Priority Data

Apr. 8, 1982 [DE]  Fed. Rep. of Germany ....... 3213140
Oct. 16, 1982 [DE] Fed. Rep. of Germany ....... 3238447
Jan. 14, 1983 [DE] Fed. Rep. of Germany ....... 3301008

[51] Int. Cl.⁵ .................... A01N 43/50; A01N 43/52; C07D 401/04
[52] U.S. Cl. .......................................... 71/92; 546/15; 546/278; 548/311; 548/313; 548/314
[58] Field of Search ................. 548/311, 313, 314; 546/15, 278; 71/92

[56]         References Cited

U.S. PATENT DOCUMENTS

| | | | |
|---|---|---|---|
| 3,668,217 | 6/1972 | Fujinami et al. | 548/314 |
| 3,798,233 | 3/1974 | Akiba et al. | 548/314 |
| 3,846,441 | 11/1974 | Mine | 548/314 |
| 3,847,933 | 11/1974 | Tyler | 548/314 |
| 3,960,883 | 6/1976 | Hubele | 548/314 |
| 4,151,290 | 4/1979 | Takayama et al. | 548/314 |

FOREIGN PATENT DOCUMENTS

| | | | |
|---|---|---|---|
| 1813 | 5/1979 | European Pat. Off. | 548/314 |
| 1032258 | 6/1958 | Fed. Rep. of Germany | 548/314 |
| 2101605 | 7/1971 | Fed. Rep. of Germany | 548/314 |
| 55-31098 | 3/1980 | Japan | 548/314 |
| 0817745 | 8/1959 | United Kingdom | 548/314 |

*Primary Examiner*—Richard A. Schwartz
*Attorney, Agent, or Firm*—Sughrue, Mion, Zinn, Macpeak & Seas

[57] ABSTRACT

Novel cycloalkane-5=-spiro-hydantoins of formula

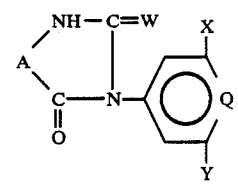

wherein A is selected from the group consisting of

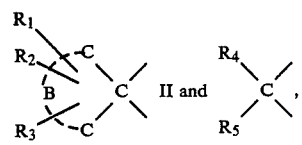

and the remaining substituents are defined below having strong, selective herbicidal activity and novel intermediates and a process for their preparation.

13 Claims, No Drawings

HERBICIDAL HYDANTOINS

This is a continuation of application Ser. No. 157,903 filed Feb. 17, 1988, now abandoned; which is a continuation of application Ser. No. 046,622 filed May 4, 1987, now abandoned; which is a continuation of application Ser. No. 856,825, filed Apr. 28, 1986, now abandoned; which is a continuation of application Ser. No. 774,901 filed Sept. 11, 1985, now abandoned; which is a continuation of application Ser. No. 623,961, filed June 25, 1984, now abandoned; which is a continuation of application Ser. No. 492,946, filed May 9, 1983, now abandoned; which is a continuation-in-part of application Ser. No. 479,709 filed Mar. 28, 1983, now abandoned.

OBJECTS OF THE INVENTION

It is an object of the invention to provide novel hydantoins of formula I and a novel process and novel intermediates for their preparation.

It is another object of the invention to provide novel herbicidal compositions and a novel method of combatting weeds.

These and other objects and advantages of the invention will become obvious from the following detailed description.

THE INVENTION

The novel compounds of the invention are cycloalkane-5'-spiro-hydantoins for formula

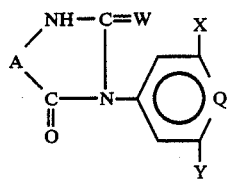

wherein A is selected from the group consisting of

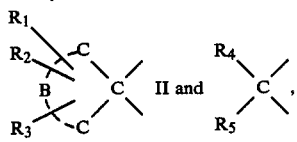

Q is selected from the group consisting of —CH— and —N—, B is a single or multiple bridged cycloalkane of 5 to 10 carbon atoms, $R_1$, $R_2$ and $R_3$ are individually selected from the groups consisting of hydrogen, alkyl of 1 to 4 carbon atoms and alkenyl of 3 to 4 carbon atoms, $R_4$ and $R_5$ are individually selected from the group consisting of alkyl of 1 to 4 carbon atoms optionally substituted with alkoxy of 1 to 4 carbon atoms of alkylthio of 1 to 4 carbon atoms, alkenyl of 2 to 4 carbon atoms, cycloalkyl of 3 to 6 carbon atoms optionally substituted with alkyl of 1 to 6 carbon atoms and phenoxy, phenylthio, phenyl and benzyl optionally substituted with at least one member of the group consisting of halogen, —$CF_3$ and alkyl and alkoxy of 1 to 4 carbon atoms, W is oxygen and when Q is —CH—, W may be sulfur and X is selected from the group consisting of halogen, hydrogen, —$CF_3$ and alkyl and alkoxy of 1 to 4 carbon atoms and Y is selected from the group consisting of halogen, —$CF_3$ and alkyl and alkoxy of 1 to 4 carbon atoms.

Halogen in the compounds of formula I includes fluorine, chlorine, bromine and iodine with chlorine being preferred. X is preferably selected from the group consisting of hydrogen, chlorine, bromine, methyl, methoxy and trifluoromethyl. Y is preferably selected from the group consisting of chlorine, bromine, methyl, methoxy and trifluoromethyl. Preferred lower alkyl and lower alkoxy are methyl, ethyl, n-propyl, isopropyl, n-butyl, isobutyl, sec.butyl, tert.butyl, methoxy, ethoxy, n-propoxy, isopropoxy, n-butoxy, isobutoxy, sec.butoxy and tert.butoxy.

$R_4$ and $R_5$ are preferably methyl, ethyl, n-propyl, isopropyl and allyl if they are alkenyl. When $R_4$ and/or $R_5$ are phenyl or benzyl, the said groups are optionally substituted with at least one member of the group consisting of alkyl and alkoxy of 1 to 4 carbon atoms, halogen and trifluoromethyl, preferably methyl, methoxy, chlorine or bromine. The A group is preferably derived from cyclohexane, cyclopentane or homologs thereof such as menthane which may contain 1 to 3 substituents like lower alkyl such as methyl or bi- or tricyclic cycloalkanes such as carane or pinane optionally substituted with 1 to 3 lower alkyls, especially methyl.

The compounds of formula I may be prepared by a variety of known processes. The compounds of formula I wherein Q is —CH— may be prepared by cyclizing (a) a carboxylic acid of the formula

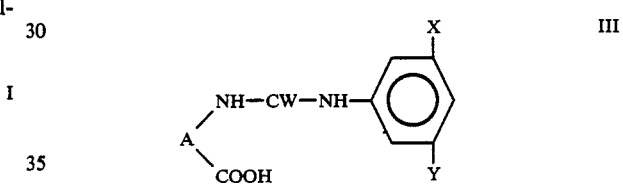

wherein A, W, X and Y are as defined above, in the presence of a strong inorganic acid, or (b) cyclizing an ester of the formula

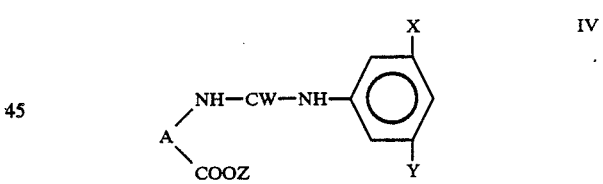

wherein A, W, X and Y are as defined above and Z is a straight-chained or branched, optionally substituted aliphatic of 1 to 20 carbon atoms or an optionally substituted araliphatic group in the presence of a base, or (c) deaminating an amino compound of the formula

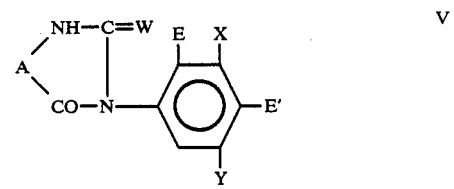

wherein A, W, X and Y are as defined above and E and E' are hydrogen or $NH_2$, at least one of these two groups being $NH_2$ to remove E and/or E'.

To prepare the compounds of formula I wherein Q is N, a spirohydantoin of the formula

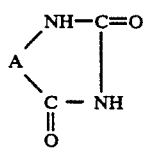

wherein A is as defined above is reacted with a pyridine of the formula

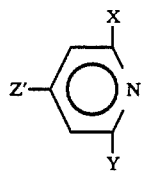

wherein X and Y are as defined above and Z' is NO$_2$ or halogen with the addition of a basic compound (e.g. potassium or sodium carbonate, potassium, sodium or calcium hydroxide) at temperatures of between about 0° and about 80° C.

The cyclizing of the acid according to process (a) is conveniently effected in an aqueous or alcoholic solution in the presence of an acid such as hydrochloric acid or sulfuric acid at elevated temperature and it is easiest to heat the mixture to reflux for some time. The cyclizing of the esters according to process (b) is preferably effected in an alcohol or another organic solvent such as dioxane and the base used is preferably a tertiary organic base, e.g. triethylamine or tripropylamine. The reaction mixture is heated, generally for some hours, at reflux. In process (c) the removal of the amino group or groups is effected in a manner known per se with diazonium compounds, for example by carrying out diazotization in the presence of refluxing ethanol [Houben-Weyl, Volume 10/3 (1965), pages 116 ff] or by adding the suspension or solution of the diazonium salt to an aqueous solution of hypophosphorous acid (loc. cit., pages 131 ff) or by carrying out diazotization with alkyl nitrites in the presence of derivatives of formic acid such as dimethylformamide (loc. cit., pages 137 ff). Process (d) can be favorably influenced by the addition of a phase transfer catalyst such as a crown ether, a tetraalkylammonium salt or a tetraalkylphosphonium salt.

The compounds of the invention may, in some cases, be present in the form of cis/trans isomers and/or in enantiomeric forms and they are assigned to the cis or trans series according to the Cahn-Ingold-Prelog system. Mixtures of geometric isomers obtained according to the invention may, if desired, subsequently be resolved, e.g. by fractional crystallization, as may racemates.

If asymmetrically substituted ketones are used to prepare the starting materials of formulae VIII and X, different geometric isomers may be formed depending on the conditions of synthesis. Finally, the isomeric cycloalkane-spirohydantoins of formula I are formed accordingly therefrom [cf. for example L. Hoyer, Chem, Ber. 83, page 491 (1950)].

The starting materials III to VII are known or may be prepared analogously to known compounds by conventional methods. To prepare the compouhnds of formula III, for example, a 1-aminocycloalkanecarboxylic acid of the formula

wherein A is as defined above is reacted with an isocyanate or isothiocyanate of the formula

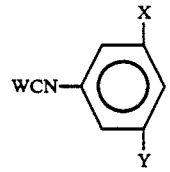

wherein W, X and Y are as defined above in aqueous or alcoholic solution at low temperatures, preferably from 0° to 10° C., in the presence of a basic substance such as sodium hydroxide solution, potassium hyroxide, solution, potassium carbonate or sodium methoxide and the compound of formula III is precipitated with a suitable acid such as hyrochloric acid, sulfuric acid or acetic acid.

The starting materials of formula IV may be obtained by reacting esters of the formula

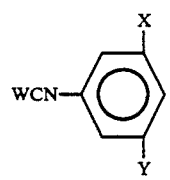

wherein A and Z are as defined above with an isocyanate or isothiocyanate of formula IX. The reactants IX and X are reacted in an inert solvent such as ether, methylene chloride, toluene or ethyl acetate at low temperatures, preferably 10° to 20° C. Z is generally a lower to medium alkyl of 1 to 12 carbon atoms or an optionally substituted benzyl group. The nature of the group is not normally critical provided that it does not lead to side reactions or inhibit the reaction by an unfavorable structure or reactive substituents.

The starting materials for process (c) may be obtained as follows, for example:

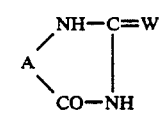

wherein A and W are as defined above is reacted with a halonitrobenzene of the formula

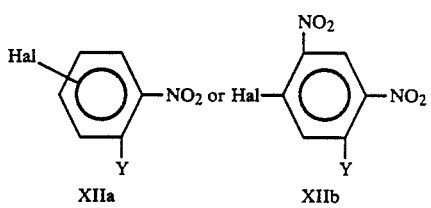

wherein Hal is fluorine or chlorine in the 2- or 4-position and Y is as defined above in the presence of a base such as K$_2$CO$_3$, Na$_2$CO$_3$, KOH, NaOH, etc. in a suitable solvent such as dimethylsulfoxide, acetonitrile or acetone, optionally with the addition of a phase transfer catalyst (crown ethers, tetraalkylammionium salts, tetraalkylphosphonium salts) at temperatures of between 0° and 150° C. to yield compounds of the formula

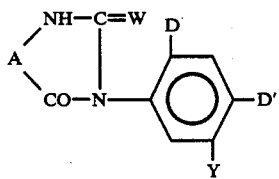

XIII wherein A, W and Y are as defined above and D and D' are H or $NO_2$, but at least one is $NO_2$.

The compounds of formula XIII are reduced to form the corresponding amino compounds of the formula

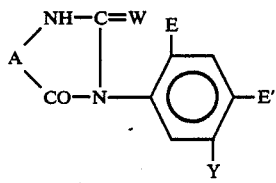

Va wherein A, W and Y are as defined above and E and E' are H or $NH_2$ but at least one is $NH_2$. These amino compounds themselves or the halogenation products thereof after halogenation with, for example, $Cl_2$, $SO_2Cl_2$, $Br_2$, compounds of formula V wherein X is chlorine or bromine, are then deaminated according to process (c).

The novel heribicidal compositions of the invention are comprised of a herbicidally effective amount of at least one compound of formula I and an inert carrier. The compositions may be in the form of granulates, dusting agents, suspension powders, concentrates or water-dispersible granulates prepared in the usual fashion.

The compositions may be prepared by mixing or grinding the active substances of formula I with diluents or extenders such as solvents and/or solid carriers, optionally with the addition of surface-active agents such as emulsifiers or dispersants and/or stabilizing and/or anti-foaming agents and possibly other additives.

The preferred solvent is water and examples of suitable solid carriers include, for example, mineral powders such as kaolines, clays, talc, chalk, quartz, highly dispersed silicic acid, aluminum oxide and silicates. Carriers which are suitable for granulates include, on the one hand, broken and fractionated rock such as calcite, marble or pumice and granulates of organic material such as sawdust, coconut shells and corn-cobs. Suitable emulsifiers include non-ionic and anionic compounds such as polyoxyethylene-fatty acid esters, polyoxyethylene fatty alcohol ethers, e.g. alkylarylpolyglycol ethers, alkylsulfonates, alkylsulfates, arylsulfonates and protein hydrolysates. The dispersant may be, for example, a waste sulfite liquor from wood processing or methyl cellulose, while the antifoaming agent may be a branched higher alcohol.

The concentrated preparations, which generally contain between 0.1 and 95% by weight, preferably between 0.5 and 90% by weight of active substance, may optionally be made into spraying or pouring liquors by diluting them with water to give the desired concentration.

The compositions of the invention are distinguished by their powerful activity against numerous weeds, particularly monocotyledons and they are preferably applied pre-emergence. As the active compounds of formula I are well tolerated, they may be used in numerous crops such as soybeans, rice, cotton, barley, beet, potatoes, tomatoes or onions.

It is often advantageous to apply combinations of the compounds of formula I with known herbicides. Examples include combinations with urea derivatives (e.g. chlortoluron), triazine derivatives (e.g. atrazine, simazine), dinitroaniline derivatives (e.g. trifluralin), chloroacetanilide derivatives (e.g. alachlor), thiocarbamates (e.g. thiobencarb) and diphenyl ethers (e.g. acifluorfen).

The novel method of the invention for combatting weeds comprises contacting weeds with a herbicidally effective amount of at least one compound of formula I. The said compounds may be applied pre- or post-emergence and can be applied by pouring, spraying, sprinkling or dusting. Depending on the compound, the particular weed and application conditions, the usual useful amount of the active compound is 0.1 to 10 kg/ha, particularly 0.3 to 3 kg/ha.

In the following examples there are described several preferred embodiments to illustrate the invention. However, it should be understood that the invention is not intended to be limited to the specific embodiments.

EXAMPLE 1

Cyclohexane-5'-spiro-3'-(3,5-dichlorophenyl)-hydantoin 171 g (1 mol) of ethyl 1-amino-cyclohexanecarboxylate prepared by esterifying 1-amino-cyclohexanecarboxylic acid with HCl/EtOH were dissolved in 500 ml of ether and a solution of 188.5 g (1 mol) of 3,5-dichlorophenylisocyanate in 500 ml of ether was introduced over 15 minutes while cooling with ice. After all the solution had been added, the resulting mixture was stirred for 30 minutes at ambient temperature and then was vacuum filtered. The filter residue was then suspended in 500 ml of ethanol and, after the addition of 10.1 g (0.1 mol) of triethylamine, it was refluxed for 3 hours and poured into 2 liters of ice water. The precipitate formed was vacuum filtered and was washed thoroughly with water and dried in a circulating air drier to obtain 280 g (89% of theory) of the title compound melting at 210°–211° C. (from ethanol).

EXAMPLE 2 cis-2-Methylcyclohexane-5'-spiro-3'-(3,5-dichlorophenyl)-2'-thio-hydantoin 11.5 g (0.5 mol) of sodium were dissolved in 500 ml of ethanol and 79 g (0.5 mol) of cis-1-amino-2-methylcyclohexane carboxylic acid were added to the solution. Then, finely powdered 3,5-dichlorophenyl isothiocyanate was added to the resulting suspension over 30 minutes and the now clear solution was stirred for 3 hours at ambient temperature and refluxed for 3 hours. It was poured into 2 liters of ice water and the precipitate formed was vacuum filtered and washed thoroughly with water and after drying, 140 g (82% of theory) of the title compound melting at 237°–239° C. (from ethanol) were obtained. Stereochemical assignment (cis or trans) was effected in accordance with the Cahn-Ingold-Prelog system.

The starting materials of formulae III and IV for the following examples were prepared by the procedures discussed above and are reported in the following Table.

| No. | A | W | X | Y | Z | Mp. [°C.] |
|---|---|---|---|---|---|---|
| 1 | cyclohexyl (gem-dimethyl) | O | Cl | Cl | C₂H₅ | 178–179 |
| 2 | cyclohexyl (gem-dimethyl) | O | Cl | Cl | H | 195–197 |
| 3 | cyclohexyl (gem-dimethyl) | O | CH₃ | CH₃ | H | 186–188 |
| 4 | cyclopentyl (gem-dimethyl) | O | Cl | Cl | H | 163–164 |
| 5 | cyclohexyl (gem-dimethyl) | O | H | CF₃ | C₂H₅ | 131–132 |
| 6 | cyclohexyl (gem-dimethyl) | O | H | CH₃ | C₂H₅ | 135–136 |
| 7 | 2-CH₃ cyclohexyl (gem-dimethyl) (2-cis) | O | Cl | Cl | H | 175–177 |
| 8 | 2-CH₃ cyclohexyl (gem-dimethyl) (2-cis) | O | Cl | Cl | C₂H₅ | 188–189 |
| 9 | 2-CH₃ cyclohexyl (gem-dimethyl) (2-cis) | O | CH₃ | CH₃ | H | 188–190 |
| 10 | adamantyl-type | O | Cl | Cl | H | 238–240 |
| 11 | cyclopentyl (gem-dimethyl) | O | Cl | Cl | C₂H₅ | 186–187 |
| 12 | 2-d(cis, trans mixture) CH₃/H₃C-CH₃ cyclohexyl (gem-dimethyl) | O | Cl | Cl | H | 172–174 |

Using the procedure of Example 1, the following compounds of formula I described in Table I were prepared:

TABLE I

| No. | A | W | X | Y | Mp. [°C.] |
|---|---|---|---|---|---|
| 1 | cyclohexyl (gem-dimethyl) | O | CH₃ | CH₃ | 224–226 |
| 2 | cyclohexyl (gem-dimethyl) | S | Cl | Cl | 225–227 |
| 3 | cyclohexyl (gem-dimethyl) | O | H | CH₃ | 198–199 |
| 4 | cyclohexyl (gem-dimethyl) | O | H | CF₃ | 222–223 |
| 5 | cyclopentyl (gem-dimethyl) | O | Cl | Cl | 134–135 |
| 6 | 2-CH₃ cyclohexyl (gem-dimethyl) (2-cis) | O | Cl | Cl | 205–206 |
| 7 | 2-CH₃ cyclohexyl (gem-dimethyl) (2-cis) | O | CH₃ | CH₃ | 202–203 |
| 8 | cyclohexyl (gem-dimethyl) | O | Cl | Cl | 258–263 |
| 9 | 4-CH₃ cyclohexyl (gem-dimethyl) (4-cis) | O | Cl | Cl | 253–255 |

TABLE I-continued

| No. | A | W | X | Y | Mp. [°C.] |
|---|---|---|---|---|---|
| 10 | CH3, H3C-CH3 (cyclohexane, 2-d-(cis,trans mixture)) | O | Cl | Cl | 207–208 |
| 11 | C2H5 cyclohexane (cis/trans) | O | Cl | Cl | |
| 12 | C2H5 cyclohexane (cis/trans) | O | CH3 | Cl | |
| 13 | C2H5 cyclohexane (cis) | O | Br | Cl | |
| 14 | C2H5 cyclohexane (cis) | O | CF3 | CF3 | |
| 15 | C2H5 cyclohexane (cis) | O | OCH3 | OCH3 | |
| 16 | C2H5 cyclohexane (trans) | S | Cl | Cl | |
| 17 | C2H5 cyclohexane (cis) | S | CH3 | CH3 | |
| 18 | CH(CH3)2 cyclohexane (cis/trans) | O | Cl | Cl | |
| 19 | CH(CH3)2 cyclohexane (cis) | S | Br | Br | |
| 20 | CH(CH3)2 cyclohexane (trans) | O | CH3 | OCH3 | |
| 21 | CH(CH3)2 cyclohexane (trans) | S | OCH3 | OCH3 | |
| 22 | CH(CH3)2 cyclohexane (cis) | S | CF3 | CF3 | |
| 23 | C4H9 cyclohexane (cis) | O | Cl | Cl | |
| 24 | C4H9 cyclohexane (trans) | O | CF3 | CF3 | |
| 25 | C4H9 cyclohexane (cis/trans) | O | CH3 | CH3 | |
| 26 | C4H9 cyclohexane (cis/trans) | O | OCH3 | OCH3 | |
| 27 | C4H9 cyclohexane (cis) | S | CH3 | OCH3 | |
| 28 | C4H9 cyclohexane (cis) | S | Cl | Cl | |
| 29 | CH2—CH=CH2 cyclohexane (cis) | O | Cl | Cl | |
| 30 | CH2—CH=CH2 cyclohexane (cis) | O | CH3 | Cl | |

TABLE I-continued

| No. | A | W | X | Y | Mp. [°C.] |
|---|---|---|---|---|---|
| 31 | CH₂—CH=CH₂, cyclohexyl (trans) | O | CF₃ | Cl | |
| 32 | CH₂—CH=CH₂, cyclohexyl (trans) | S | OCH₃ | OCH₃ | |
| 33 | CH₂—CH=CH₂, cyclohexyl (cis) | S | CF₃ | CF₃ | |
| 34 | CH₂—CH=CH₂, cyclohexyl, CH₂—CH=CH₂ (2-trans) | O | Cl | Cl | |
| 35 | CH₂—CH=CH₂, cyclohexyl, CH₂—CH=CH₂ (2-trans) | O | Br | Br | |
| 36 | CH₂—CH=CH₂, cyclohexyl, CH₂—CH=CH₂ (2-cis) | S | CF₃ | CF₃ | |
| 37 | CH₂—CH=CH₂, cyclohexyl, CH₂—CH=CH₂ (2-cis) | S | Cl | Cl | |
| 38 | CH₃, cyclopentyl, H₃C, CH₃ (trans) | O | Cl | Cl | |
| 39 | CH₃, cyclopentyl, H₃C, CH₃ (cis) | O | Cl | Cl | |
| 40 | CH₃, cyclopentyl, H₃C, CH₃ (cis) | S | Cl | Br | |
| 41 | CH₃, cyclopentyl, H₃C, CH₃ (cis) | S | CH₃ | CH₃ | |
| 42 | CH₃, cyclopentyl, H₃C, CH₃ (trans) | O | CH₃ | Cl | |
| 43 | CH₃, cyclopentyl, H₃C, CH₃ (cis) | O | OCH₃ | OCH₃ | |
| 44 | CH₃, cyclopentyl, H₃C, CH₃ (trans) | O | CF₃ | CF₃ | |
| 45 | CH₃, cyclohexyl, CH₃ (trans) | O | Br | Br | |
| 46 | CH₃, cyclohexyl, CH₃ (cis) | O | CH₃ | CH₃ | |
| 47 | CH₃, cyclohexyl, CH₃ (cis) | O | CF₃ | CF₃ | |

TABLE I-continued

| No. | A | W | X | Y | Mp. [°C] |
|-----|---|---|---|---|----------|
| 48 | CH₃–cyclohexyl–CH₃ (trans) | O | OCH₃ | OCH₃ | |
| 49 | CH₃–cyclohexyl–CH₃ (cis) | S | Cl | Cl | |
| 50 | CH₃–cyclohexyl–CH₃ (trans) | S | Cl | Br | |

EXAMPLE 3 cis-4-Methylcyclohexane-5'-spiro-3'-(3,5-dibromophenyl)hydantoin

STEP A:

cis-4-methylcyclohexane-5'-spiro-3'-(2-nitrophenyl)-hydantoin 18.2 g (0.1 mol) of cis-4-methylcyclohexane-5'-spirohydantoin, 18 g (0.1 mol) of 2-nitro-chlorobenzene and 41.4 g (0.3 mol) of potassium carbonate were dissolved or suspended in 100 ml of dimethylformamide and the mixture was then stirred for 5 hours at about 120° C. The mixture was then poured onto ice and the precipitate formed was vacuum filtered, washed thoroughly with water and crystallized from acetonitrile to obtain 15.5 g (51% of theory) of title compound melting at 227°–229° C.

STEP B:

cis-4-methylcyclohexane-5'-spiro-3'-(2-aminophenyl)-hydantoin 15.2 g (0.05 mol) of cis-4-methylcyclohexane-5'-spiro-3'-(2-nitrophenyl)-hydantoin were dissolved in 200 ml of methanol and 5 ml of conc. hydrochloric acid and, after the addition of 4 g of catalyst (Pd/C, 10%), the mixture was hydrogenated at a maximum temperature of 40° C. and under a pressure of 5 bar. After hydrogen absorption ceased, the catalyst was removed by vacuum filtration and the mother liquor was concentrated by evaporation. The residue was taken up in water and the solution was neutralized with sodium bicarbonate. The solid product obtained was vacuum filtered, washed with water and crystallized from isopropanol to obtain 11.5 g (84% of theory) of the title compound melting at 255°–256° C.

STEP C:

cis-4-Methylcyclohexane-5'-spiro-3'-(2-amino-3,5-dibromophenyl)hydantoin 27.33 g (0.1 mol) of cis-4-methyl-cyclohexane-5'-spiro-3'-(2-amino-phenyl)hydantoin were dissolved in 200 ml of glacial acetic acid and a solution of 32 g (0.2 mol) of bromine in 50 ml of glacial acetic acid was added thereto dropwise over 30 minutes at ambient temperature. The resulting mixture was stirred for about 30 minutes, then was diluted with 1 liter of water and the precipitate was vacuum filtered. The product was washed with water and crystallized from acetonitrile to obtain 35.4 g (82% of theory) of the title compound melting at 264°–266° C.

STEP D:

cis-4-Methylcyclohexane-5'-spiro-3'-(3,5-dibromophenyl)-hydantoin 21.6 g (0.05 mol) of cis-4-methyl-5'-spiro-3'-(2-amino-3,5-dibromophenyl)-hydantoin were dissolved in 300 ml of ethanol and 10 ml of conc. sulfuric acid and the mixture was heated to reflux. Then, 3.8 g (0.055 mol) of sodium nitrite were added thereto in batches over about 20 minutes and the resulting mixture was refluxed for 1 hour with stirring. After it had cooled, it was diluted with 1 liter of ice water and the resulting precipitate was vacuum filtered, washed with water and crystallized from acetonitrile to obtain 12.3 g (59% of theory) of the title compound melting at 247°–249° C.

EXAMPLE 4 cis-2-Ethylcyclohexane-5'-spiro-3'-(3,5-dibromophenyl)-hydantoin (a)

cis-2-ethylcyclohexane-4'-spiro-3'-(2,4-dinitrophenyl)-hydantoin 39 g (0.2 mol) of cis-2-ethylcyclohexane-5'-spirohydantoin, 40.4 g (0.2 mol) of 1-chloro-2,4-dinitrobenzene, 83 g (0.6 mol) of potassium carbonate and 1 g of tetrabutylammonium hydrogen sulfate were stirred into 200 ml of dimethylsulfoxide at 10° C. for 6 hours and the mixture was then diluted with 500 ml of water. The mixture was vacuum filtered, and the product was washed with water and cold methanol and dried to obtain 62.4 g (86% of theory) of title compound melting at 231°–232° C.

(b)

cis-2-ethylcyclohexane-5'-spiro-3'-(2,4-diaminophenyl)-hydantoin 36.2 g (0.1 mol) of cis-2-ethylcyclohexane-5'-spiro-3'-(2,4-dinitrophenyl)-hydantoin were dissolved in 500 ml of methanol and 20 ml of conc. hydrochloric acid and after 10 g of catalyst (10% Pd/C) were added thereto, the mixture was hydrogenated at a temperature of not more than 65° C. under a pressure of 5 bar. Then the catalyst was removed by vacuum filtering and the filtrate was concentrated by evaporation. The residue was taken up in water and the solution was neutralized with sodium bicarbonate. The precipitate formed was vacuum filtered, washed with water and crystallized from isopropanol to obtain 25.4 g (84% of theory) of title compound melting at 183°–185° C.

(c)

cis-2-Ethylcyclohexane-5'-spiro-4'-(2,4-diamino-3,5-dibromophenyl)-hydantoin 15 g (0.05 mol) of cis-2-ethylcyclohexane-5'-spiro-3'-(2,4-diaminophenyl)-hydantoin were dissolved in 100 ml of glacial acetic acid and a solution of 5.06 g (0.1 mol) of bromine in 20 ml of glacial acetic acid was added dropwise thereto at ambient temperature over 10 minutes. The resulting mixture was stirred for another 20 minutes, then 300 ml of ice water were added. The solid matter was separated by vacuum filtration and was washed thoroughly with water and dried in vacuo to obtain 18 g (78.3% of theory) of title compound melting at 263°–265° C.

(d) cis-2-Ethylcyclohexane-5'-spiro-3'-(3,5-dibromophenyl)-hydantoin

A solution of 3.5 g (0.03 mol) of isoamyl nitrite in 50 ml of dimethylformamide was heated to 55° C. and at this temperature, a solution of 6.9 g (0.015 mol) of cis-2-ethyl-cyclohexane-5'-spiro-3'-(2,4-diamino-3,5-dibromopenyl)-hydantoin in 20 ml of dimethylformamide was added dropwise thereto over 1 hour. The temperature was then raised to 70°–80° C. until the development of nitrogen gas ceased. The mixture was then concentrated by evaporation in vacuo and the dark residue was purified by column chromatography (silica gel/ethyl acetate) to obtain 3.9 g (59% of theory) of title compound melting at 213°–215° C.

Using the procedure of Examples 3 and 4, the compounds of Table II were prepared by selection of the appropriate starting materials.

TABLE II

| No. | A | W | X | Y | Mp °C. |
|---|---|---|---|---|---|
| 1 | CH₃-cyclohexyl (cis) | O | Br | CH₃ | 193–195 |
| 2 | CH₃-cyclohexyl (cis) | O | Cl | CH₃ | 202–203 |
| 3 | C₂H₅-cyclohexyl (cis) | O | Cl | Cl | 193–195 |
| 4 | H₃C,CH₃/H₃C,CH₃-cyclohexyl | O | Cl | Cl | 212–213 |
| 5 | C₂H₅-cyclohexyl (cis) | O | CH₃ | CH₃ | 162–163 |
| 6 | H₃C-cyclohexyl | O | CH₃ | CH₃ | 208–211 |
| 7 | CH₃-cyclohexyl (trans) | O | Cl | Cl | 188–189 |
| 8 | CH₃-cyclohexyl (cis) | O | OCH₃ | OCH₃ | 177–179 |
| 9 | CH₃-cyclohexyl (cis) | O | CF₃ | CF₃ | 179–181 |

EXAMPLE 5 cis-2-Methylcyclohexane-5'-spiro-3'-(2,6-dichloropyridyl-4)-hydantoin 192 g (1 mol) of cis-2-methylcyclohexane-5'-spirohydantoin, 194 g (1 mol) of 2,6-dichloro-4-nitropyridine, 207 g (1.5 mol) of potassium carbonate and 3.4 g (0.01 mol) of tetrabutylammonium hydrogen sulfate were dissolved or suspended in 1000 ml of dimethylsulfoxide at ambient temperature and the mixture was then stirred at 15°–20° C. for another 16 hours. Then, about 5000 ml of ice water were introduced and the precipitate formed was vacuum filtered, washed thoroughly with water and recrystallized from acetonitrile to obtain 250 g (79% of theory) of title compound melting at 227°–229° C.

Using the procedure of Example 5, the compounds listed in Table III were prepared by selection of the appropriate starting materials.

TABLE III

| No. | A | X | Y | Mp °C. |
|---|---|---|---|---|
| 1 | C(CH₃)₃-cyclohexyl -cis- | Cl | Cl | 216–218 |
| 2 | CH(CH₃)₂-cyclohexyl -cis- | Cl | Cl | 190–191 |
| 3 | CH₂—CH=CH₂-cyclohexyl -cis- | Cl | Cl | 138–140 |
| 4 | C₂H₅-cyclohexyl -cis- | Cl | Cl | 191–193 |

TABLE III-continued

| No. | A | X | Y | Mp °C |
|---|---|---|---|---|
| 5 | cyclohexane with CH$_2$—CH=CH$_2$ and CH$_2$—CH=CH$_2$ substituents -cis- | Cl | Cl | 125–127 |
| 6 | cyclohexane with CH$_3$, CH$_3$ substituents, mixture of isomers | Cl | Cl | 238–242 |

EXAMPLE 6

5-Methyl-5-cyclopropyl-3-[4-(2,6-dichloropyridyl)]-hydantoin

A suspension consisting of 3.1 g of 5-methyl-5-cyclopropyl-hydantoin, 3.86 g of 2,6-dichloro-4-nitropyridine and 5.6 g of potassium carbonate in 10 ml of dimethylformamide was stirred for 18 hours at 20° C. and then was added to 100 ml of water. After 30 minutes of stirring, the resulting precipitate was vacuum filtered and taken up in methylene chloride. After drying and removal of the solvent, 3.2 g (64% of theory) of 5-methyl-5-cyclopropyl-3-[4-(2,6-dichloropyridyl)]-hydantoin melting at 160° C. (reprecipitated from toluene/petroleum ether) were obtained.

EXAMPLE 7

5-Methyl-5-cyclopropyl-3-(3,5-dimethylphenyl)-hydantoin 0.3 g of triethylamine were added to a solution of 0.8 g of methyl 1-(3,5-dimethylphenyl)-3-[2-(2-cyclopropyl)propanoate]-urea in 30 ml of methanol and the mixture was refluxed for 12 hours. After the solvent had been removed, the residue was triturated with petroleum ether and the crystalline precipitate obtained was vacuum filtered to obtain 0.6 g (85% of theory) of title compound melting at 121° C.

EXAMPLE 8

5-n-Propyl-5-(1-methylethyl)-3-(3,5-dichlorophenyl)-2-thio-hydantoin

A solution of 2.0 g of 3,5-dichlorophenyl isothiocyanate in 10 ml of absolute tetrahydrofuran was added dropwise at 20° C. to a solution of 1.7 g of methyl 2-amino-2-(1-methylethyl)-pentanoate in 10 ml of absolute tetrahydrofuran and the mixture was stirred at 20° C. for a further 4 hours. Then the solvent was removed and the residue was recyrstallized from diisopropyl ether to obtain 1.6 g (46% of theory) of title compound melting at 160° C.

Using the procedure of Example 7 and 8, the compounds of Table IV were prepared by selection of the appropriate starting materials.

TABLE IV

End products of formula I (A represents $\overset{R_4}{\underset{R_5}{\diagdown}}C=$)

| No. | Q | W | X | Y | R$_4$ | R$_5$ | Mp [°C.] |
|---|---|---|---|---|---|---|---|
| 1 | N | O | Cl | Cl | CH$_3$ | i-C$_3$H$_7$ | 129 |
| 2 | N | O | Cl | Cl | i-C$_3$H$_7$ | i-C$_3$H$_7$ | 157–159 |
| 3 | N | O | Cl | Cl | CH$_3$ | t-C$_4$H$_9$ | 167–170 |
| 4 | N | O | Cl | Cl | n-C$_3$H$_7$ | i-C$_3$H$_7$ | 91–93 |
| 5 | N | O | Cl | Cl | CH$_3$ | —CH$_2$—CH$_2$—CH=CH$_2$ | 76–81 |
| 6 | N | O | Cl | Cl | C$_2$H$_5$ | i-C$_3$H$_7$ | 97–103 |
| 7 | N | O | Cl | Cl | C$_6$H$_5$ | C$_6$H$_5$ | 190–194 |
| 8 | N | O | Cl | Cl | CH$_3$ | C$_6$H$_5$ | 167–170 |
| 9 | N | O | Cl | Cl | CH$_3$ | n-C$_4$H$_9$ | |
| 10 | N | O | Cl | Cl | CH$_3$ | 2-methylphenyl | 161–163 |
| 11 | N | O | Cl | Cl | CH$_3$ | C$_2$H$_5$ | |
| 12 | N | O | Cl | Cl | CH$_3$ | i-C$_4$H$_9$ | 133–138 |
| 13 | N | O | Cl | Cl | CH$_3$ | s-C$_4$H$_9$ | 105–112 |
| 14 | N | O | Cl | Cl | C$_2$H$_5$ | t-C$_4$H$_9$ | |
| 15 | CH | O | Cl | Cl | CH$_3$ | CH$_3$ | 159–161 |
| 16 | CH | O | Cl | Cl | CH$_3$ | i-C$_3$H$_7$ | 124 |
| 17 | CH | S | Cl | Cl | CH$_3$ | i-C$_3$H$_7$ | 168 |
| 18 | CH | O | CH$_3$ | CH$_3$ | CH$_3$ | i-C$_3$H$_7$ | 134–136 |
| 19 | CH | S | CH$_3$ | CH$_3$ | CH$_3$ | i-C$_3$H$_7$ | 150 |
| 20 | CH | O | Cl | Cl | CH$_3$ | cyclopropyl | 145 |
| 21 | CH | S | Cl | Cl | CH$_3$ | cyclopropyl | 121 |

TABLE IV-continued

End products of formula I (A represents $\begin{array}{c}R_4\\ \diagdown\\ \diagup\\ R_5\end{array} C{=\!\!=}$)

| No. | Q | W | X | Y | R$_4$ | R$_5$ | Mp [°C.] |
|---|---|---|---|---|---|---|---|
| 22 | CH | S | CH$_3$ | CH$_3$ | CH$_3$ |  | 175 |
| 23 | CH | O | Cl | Cl | CH$_3$ | t-C$_4$H$_9$ | 230 |
| 24 | CH | O | CH$_3$ | CH$_3$ | CH$_3$ | t-C$_4$H$_9$ | 153 |
| 25 | CH | S | Cl | Cl | CH$_3$ | t-C$_4$H$_9$ | 207 |
| 26 | CH | O | Cl | Cl | n-C$_3$H$_7$ | i-C$_3$H$_7$ | 140–145 |
| 27 | CH | O | CH$_3$ | CH$_3$ | n-C$_3$H$_7$ | i-C$_3$H$_7$ | 110 |
| 28 | CH | O | Cl | Cl | CH$_3$ | —CH$_2$—CH$_2$—CH=CH$_2$ | 80 |
| 29 | CH | O | Cl | Cl | CH$_3$ | n-C$_4$H$_9$ | 100 |
| 30 | CH | O | CH$_3$ | CH$_3$ | CH$_3$ | n-C$_4$H$_9$ | 122 |
| 31 | CH | O | CH$_3$ | CH$_3$ | CH$_3$ | —CH$_2$—CH$_2$—CH=CH$_2$ | 90 |
| 32 | CH | S | Cl | Cl | CH$_3$ | —CH$_2$—CH$_2$—CH=CH$_2$ | 157 |
| 33 | CH | S | Cl | Cl | CH$_3$ | n-C$_4$H$_9$ | 168 |
| 34 | CH | O | Cl | Cl | CH$_3$ | C$_6$H$_5$ | 158 |
| 35 | CH | O | CH$_3$ | CH$_3$ | CH$_3$ | C$_6$H$_5$ | 168 |
| 36 | CH | O | Cl | Cl | C$_6$H$_5$ | C$_6$H$_5$ | 136 |
| 37 | CH | O | CH$_3$ | CH$_3$ | C$_6$H$_5$ | C$_6$H$_5$ | |
| 38 | CH | S | Cl | Cl | CH$_3$ | C$_6$H$_5$ | 190 |
| 39 | CH | S | Cl | Cl | C$_6$H$_5$ | C$_6$H$_5$ | |
| 40 | CH | O | Cl | Cl | CH$_3$ | 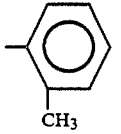 | 205 |
| 41 | CH | O | CH$_3$ | CH$_3$ | CH$_3$ | 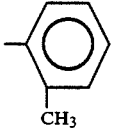 | |
| 42 | CH | S | Cl | Cl | CH$_3$ | 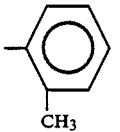 | |
| 43 | CH | O | Cl | Cl | i-C$_3$H$_7$ | i-C$_3$H$_7$ | 210 |
| 44 | CH | O | CH$_3$ | CH$_3$ | i-C$_3$H$_7$ | i-C$_3$H$_7$ | |
| 45 | CH | S | Cl | Cl | i-C$_3$H$_7$ | i-C$_3$H$_7$ | amorphous |
| 46 | CH | O | Cl | Cl | CH$_3$ | C$_2$H$_5$ | |
| 47 | CH | O | CH$_3$ | CH$_3$ | CH$_3$ | C$_2$H$_5$ | |
| 48 | CH | S | Cl | Cl | CH$_3$ | C$_2$H$_5$ | |
| 49 | CH | O | Cl | Cl | CH$_3$ | i-C$_4$H$_9$ | |
| 50 | CH | O | CH$_3$ | CH$_3$ | CH$_3$ | i-C$_4$H$_9$ | |
| 51 | CH | S | Cl | Cl | CH$_3$ | i-C$_4$H$_9$ | 144 |
| 52 | CH | O | Cl | Cl | C$_2$H$_5$ | i-C$_3$H$_7$ | |
| 53 | CH | O | CH$_3$ | CH$_3$ | C$_2$H$_5$ | i-C$_3$H$_7$ | |
| 54 | CH | S | Cl | Cl | C$_2$H$_5$ | i-C$_3$H$_7$ | |
| 55 | CH | O | Cl | Cl | CH$_3$ | s-C$_4$H$_9$ | 130 |
| 56 | CH | O | CH$_3$ | CH$_3$ | CH$_3$ | s-C$_4$H$_9$ | |
| 57 | CH | S | Cl | Cl | CH$_3$ | s-C$_4$H$_9$ | 142 |
| 58 | CH | O | Cl | Cl | C$_2$H$_5$ | t-C$_4$H$_9$ | |
| 59 | CH | O | CF$_3$ | CF$_3$ | CH$_3$ | i-C$_3$H$_7$ | 124 |
| 60 | CH | O | OCH$_3$ | OCH$_3$ | CH$_3$ | i-C$_3$H$_7$ | 129–130 |
| 61 | CH | O | Br | Br | CH$_3$ | i-C$_3$H$_7$ | 140 |
| 62 | CH | O | Cl | CH$_3$ | CH$_3$ | i-C$_3$H$_7$ | 120 |
| 63 | CH | O | Br | CH$_3$ | CH$_3$ | i-C$_3$H$_7$ | 135 |
| 64 | CH | S | OCH$_3$ | Cl | CH$_3$ | i-C$_3$H$_7$ | |
| 65 | CH | O | Cl | Br | C$_2$H$_5$ |  | |
| 66 | N | S | Cl | CH$_3$ | C$_2$H$_5$ | t-C$_4$H$_9$ | |
| 67 | N | O | OCH$_3$ | Cl | i-C$_3$H$_7$ | i-C$_3$H$_7$ | |

TABLE IV-continued

End products of formula I (A represents $\begin{array}{c}R_4\\ \phantom{a}\diagdown\\ \phantom{aa}C=\\ \phantom{a}\diagup\\ R_5\end{array}$)

| No. | Q | W | X | Y | $R_4$ | $R_5$ | Mp [°C.] |
|---|---|---|---|---|---|---|---|
| 68 | CH | O | $CF_3$ | Cl | $CH_3$ | cyclopropyl | |
| 69 | CH | S | Cl | $CH_3$ | $CH_3$ | $i-C_3H_7$ | |
| 70 | N | S | Cl | $CH_3$ | $i-C_3H_7$ | $i-C_3H_7$ | |
| 71 | CH | S | Cl | Cl | cyclopropyl | $C_6H_5$ | 146 |
| 72 | CH | S | Cl | Cl | $CH_3$ | $CH_2-O-CH_3$ | 164 |
| 73 | CH | O | Cl | Cl | $CH_3$ | $CH_2-O-CH_3$ | 134 |
| 74 | CH | O | Cl | Cl | $CH_3$ | cyclohexyl-H | 185 |
| 75 | CH | O | Cl | Cl | $C_2H_5$ | $i-C_4H_9$ | 140 |
| 76 | CH | O | Cl | Cl | $CH_3$ | $CH_2-C_6H_5$ | 142 |
| 77 | N | O | Cl | Cl | $C_6H_5$ | cyclopropyl | 137–140 |
| 78 | N | O | Cl | Cl | (2-OCH3, 4-CH3 phenyl) | | 228–233 |
| 79 | N | O | Cl | Cl | $CH_3$ | $-CH-O-CH_3$ | 156–158 |
| 80 | N | O | Cl | Cl | $CH_3$ | cyclohexyl-H | 148–155 |
| 81 | N | O | Cl | Cl | cyclopropyl | cyclopropyl | 195–199 |
| 82 | N | O | Cl | Cl | $CH_3$ | $-CH_2-O-C_6H_5$ | 128–135 |

Starting or intermediate products for the compounds of Table IV.

TABLE V

Hydantoins of formula $\begin{array}{c}R_4\\ \phantom{a}\diagdown\phantom{a}CO-NH\\ \phantom{aaa}X\phantom{aaaa}|\\ \phantom{a}\diagup\phantom{a}NH-CO\\ R_5\end{array}$

| No. | $R_4$ | $R_5$ | Mp [°C.] |
|---|---|---|---|
| 1 | $i-C_3H_7$ | $CH_3$ | 176–177 |
| 2 | $t-C_4H_9$ | $CH_3$ | 220 |
| 3 | cyclopropyl | $CH_3$ | 149–150 |
| 4 | $CH_2=CH-CH_2-CH_2$ | $CH_3$ | 117 |
| 5 | $n-C_3H_7$ | $i-C_3H_7$ | 188 |
| 6 | $i-C_3H_7$ | $i-C_3H_7$ | 210–212 |
| 7 | $n-C_4H_9$ | $CH_3$ | 105–106 |
| 8 | $C_6H_5$ | $CH_3$ | 200 |
| 9 | $C_6H_5$ | $C_6H_5$ | 300 |
| 10 | $C_3H_7$ | $CH_3$ | 124–126 |
| 11 | $i-C_4H_9$ | $CH_3$ | 147 |
| 12 | $i-C_3H_7$ | $C_2H_5$ | |
| 13 | $t-C_4H_9$ | $C_2H_5$ | |
| 14 | $s-C_4H_9$ | $CH_3$ | 179–189 |

TABLE V-continued

Hydantoins of formula $$\begin{array}{c} R_4 \\ \diagdown \\ R_5 \end{array} \begin{array}{c} CO-NH \\ \diagup \\ \diagdown \\ NH-CO \end{array}$$

| No. | R$_4$ | R$_5$ | Mp [°C.] |
|---|---|---|---|
| 15 | 2-CH$_3$-C$_6$H$_4$ (o-tolyl) | CH$_3$ | 158 |
| 16 | cyclopropyl | cyclopropyl | 199–200 |
| 17 | CH$_2$—O—CH$_3$ | CH$_3$ | 170–173 |
| 18 | cyclopropyl | —C$_6$H$_5$ | 214 |
| 19 | CH$_3$ | 2-OCH$_3$-C$_6$H$_4$ | 226–228 |
| 20 | C$_6$H$_5$ | 2-Cl-C$_6$H$_4$ | >250 |

TABLE VI

Aminocarboxylic acid hydrochlorides of the formula $$HOOC-\underset{R_3}{\overset{R_4}{\underset{|}{\overset{|}{C}}}}-NH_2 \cdot HCl$$

| No. | R$_4$ | R$_5$ | Mp. [°C.] |
|---|---|---|---|
| 1 | t-C$_4$H$_9$ | CH$_3$ | 250 |
| 2 | i-C$_3$H$_7$ | CH$_3$ | 250 |
| 3 | cyclopropyl | CH$_3$ | ca. 255 |
| 4 | CH$_2$=CH—CH$_2$—CH$_2$ | CH$_3$ | 250 |
| 5 | CH$_3$—CH$_2$—CH$_2$ | i-C$_3$H$_7$ | ca. 230 |
| 6 | i-C$_3$H$_7$ | i-C$_3$H$_7$ | |
| 7 | n-C$_4$H$_9$ | CH$_3$ | 230 |
| 8 | C$_6$H$_5$ | CH$_3$ | >250 |
| 9 | C$_6$H$_5$ | C$_6$H$_5$ | >250 |
| 10 | 2-CH$_3$-C$_6$H$_4$ | CH$_3$ | amorphous |
| 11 | C$_3$H$_7$ | CH$_3$ | |
| 12 | i-C$_4$H$_9$ | CH$_3$ | |
| 13 | i-C$_4$H$_7$ | C$_2$H$_5$ | |
| 14 | t-C$_4$H$_9$ | C$_2$H$_5$ | |
| 15 | s-C$_4$H$_9$ | CH$_3$ | 215 |
| 16 | cyclopropyl | C$_6$H$_5$ | 240 |
| 17 | CH$_3$ | 2-OCH$_3$-C$_6$H$_4$ | >220 |
| 18 | cyclopropyl | cyclopropyl | >250 |

TABLE VII

Aminocarboxylic acid derivatives $$ZOOC-\underset{R_5}{\overset{R_4}{\underset{|}{\overset{|}{C}}}}-NH_2$$

| No. | R$_4$ | R$_5$ | Z | Physical data mp [°C.] |
|---|---|---|---|---|
| 1 | i-C$_3$H$_7$ | CH$_3$ | CH$_3$ | Bp. 69–70° C./ 21 mbar |
| 2 | t-C$_4$H$_9$ | CH$_3$ | CH$_3$ | |
| 3 | | CH$_3$ | CH$_3$ | |
| 4 | CH$_2$=CH—CH$_2$—CH$_2$ | CH$_3$ | CH$_3$ | |
| 5 | n-C$_3$H$_7$ | i-C$_3$H$_7$ | CH$_3$ | |
| 6 | n-C$_4$H$_9$ | CH$_3$ | C$_2$H$_5$ | |
| 7 | C$_6$H$_5$ | CH$_3$ | CH$_3$ | |
| 8 | C$_6$H$_5$ | C$_6$H$_5$ | CH$_3$ | |
| 9 | 2-CH$_3$-C$_6$H$_4$ | CH$_3$ | CH$_3$ | |

TABLE VII-continued

Aminocarboxylic acid derivatives $$\geq OOC-\underset{R_5}{\overset{R_4}{\underset{|}{\overset{|}{C}}}}-NH_2$$

| No. | R₄ | R₅ | Z | Physical data mp [°C.] |
|-----|-----|-----|-----|-----|
| 10 | i-C₃H₇ | CH₃ | C₂H₅ | |
| 11 | i-C₃H₇ | CH₃ | i-C₃H₇ | |
| 12 | i-C₃H₇ | CH₃ | CH₂=CH—CH₂ | |
| 13 | i-C₃H₇ | CH₃ | C₆H₅ | |
| 14 | C₂H₅ | CH₃ | CH₃ | |
| 15 | i-C₄H₉ | CH₃ | CH₃ | |
| 16 | i-C₃H₇ | C₂H₅ | CH₃ | |
| 17 | s-C₄H₉ | CH₃ | CH₃ | |
| 18 | t-C₄H₉ | C₂H₅ | CH₃ | |
| 19 | CH₃ | i-C₃H₇ | n-C₄H₈—OCH₃ | |
| 20 | CH₃ | i-C₃H₇ | C₂H₄—OC₂H₅ | |

The compounds in the above Table were characterised by NMR and IR spectra.

TABLE VIII

Compounds of the formula $$\underset{Y}{\overset{X}{\text{-C}_6H_3\text{-}}}-NH-CO-NH-\underset{R_5}{\overset{R_4}{\underset{|}{\overset{|}{C}}}}-COOZ$$

| No. | X | Y | R₄ | R₅ | Z | Mp [°C.] |
|-----|-----|-----|-----|-----|-----|-----|
| 1 | Cl | Cl | CH₃ | CH₃ | C₂H₅ | 172 |
| 2 | Cl | Cl | CH₃ | i-C₃H₇ | CH₃ | 178 |
| 3 | Cl | Cl | CH₃ | cyclopropyl | CH₃ | 168 |
| 4 | Cl | Cl | CH₃ | t-C₄H₉ | CH₃ | 194 |
| 5 | Cl | Cl | n-C₃H₇ | i-C₃H₇ | CH₃ | 145 |
| 6 | Cl | Cl | CH₃ | CH₂=CH—CH₂—CH₂ | H | amorphous |
| 7 | CH₃ | CH₃ | CH₃ | i-C₃H₇ | CH₃ | 182 |
| 8 | CH₃ | CH₃ | CH₃ | cyclopropyl | CH₃ | 161 |
| 9 | CH₃ | CH₃ | CH₃ | t-C₄H₉ | CH₃ | 206 |
| 10 | Cl | Cl | CH₃ | i-C₃H₇ | C₂H₅ | 155–158 |
| 11 | Cl | Cl | CH₃ | i-C₃H₇ | i-C₃H₇ | 85–90 |
| 12 | Cl | Cl | CH₃ | i-C₃H₇ | CH₂=CH—CH₂ | 144 |
| 13 | Cl | Cl | CH₃ | i-C₃H₇ | C₆H₅ | |
| 14 | Cl | Cl | CH₃ | n-C₄H₉ | C₂H₅ | 138–140 |
| 15 | CH₃ | CH₃ | CH₃ | n-C₄H₉ | C₂H₅ | 134 |
| 16 | CH₃ | CH₃ | CH₃ | CH₂=CH—CH₂—CH₂ | H | |
| 17 | Cl | Cl | CH₃ | C₆H₅ | C₂H₅ | 180 |
| 18 | CH₃ | CH₃ | CH₃ | C₆H₅ | C₂H₅ | 185 |
| 19 | Cl | Cl | C₆H₅ | C₆H₅ | C₂H₅ | 200 |
| 20 | CH₃ | CH₃ | C₆H₅ | C₆H₅ | CH₃ | |
| 21 | Cl | Cl | CH₃ | 3-methylphenyl | C₂H₅ | 223 |
| 22 | CH₃ | CH₃ | CH₃ | 3-methylphenyl | H | 205 |

TABLE VIII-continued

Compounds of the formula

| No. | X | Y | R$_4$ | R$_5$ | Z | Mp [°C.] |
|---|---|---|---|---|---|---|
| 23 | Cl | Cl | i-C$_3$H$_7$ | i-C$_3$H$_7$ | H | 75-80 |
| 24 | CH$_3$ | CH$_3$ | i-C$_3$H$_7$ | C$_3$H$_7$ | H | |
| 25 | Cl | Cl | CH$_3$ | C$_2$H$_5$ | CH$_3$ | |
| 26 | CH$_3$ | CH$_3$ | CH$_3$ | C$_2$H$_5$ | CH$_3$ | |
| 27 | Cl | Cl | CH$_3$ | i-C$_4$H$_9$ | CH$_3$ | |
| 28 | CH$_3$ | CH$_3$ | CH$_3$ | i-C$_4$H$_9$ | CH$_3$ | |
| 29 | Cl | Cl | C$_2$H$_5$ | i-C$_3$H$_7$ | CH$_3$ | 185 |
| 30 | CH$_3$ | CH$_3$ | C$_2$H$_5$ | i-C$_3$H$_7$ | CH$_3$ | |
| 31 | Cl | Cl | CH$_3$ | s-C$_4$H$_9$ | CH$_3$ | 174-176 |
| 32 | CH$_3$ | CH$_3$ | CH$_3$ | s-C$_4$H$_9$ | CH$_3$ | |
| 33 | Cl | Cl | C$_2$H$_5$ | t-C$_4$H$_9$ | CH$_3$ | |
| 34 | CF$_3$ | CF$_3$ | CH$_3$ | i-C$_3$H$_7$ | C$_2$H$_5$ | 160 |
| 35 | OCH$_3$ | OCH$_3$ | CH$_3$ | i-C$_3$H$_7$ | C$_2$H$_5$ | 160 |
| 36 | Br | Br | CH$_3$ | i-C$_3$H$_7$ | C$_2$H$_5$ | 190 |
| 37 | CH$_3$ | Cl | CH$_3$ | 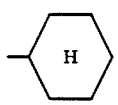 | C$_2$H$_4$—OCH$_3$ | |
| 38 | CH$_3$ | Cl | CH$_3$ | i-C$_3$H$_7$ | n-C$_4$H$_9$ | |
| 39 | Cl | OCH$_3$ | CH$_3$ | i-C$_3$H$_7$ | n-C$_4$H$_8$—OCH$_3$ | |
| 40 | Cl | CF$_3$ | CH$_3$ | i-C$_3$H$_7$ | C$_2$H$_4$—O—C$_2$H$_5$ | |
| 41 | Cl | CH$_3$ | CH$_3$ | i-C$_3$H$_7$ | C$_2$H$_5$ | 165 |
| 42 | Br | CH$_3$ | CH$_3$ | i-C$_3$H$_7$ | C$_2$H$_5$ | 172 |
| 43 | CH$_3$ | CH$_3$ | i-C$_3$H$_7$ | n-C$_4$H$_9$ | CH$_3$ | 123 |
| 44 | Cl | Cl | CH$_3$ | CH$_2$—O—CH$_3$ | CH$_3$ | 145-148 |
| 45 | Cl | Cl | CH$_3$ |  | CH$_3$ | 200-205 |
| 46 | CH$_3$ | CH$_3$ | CH$_3$ | CH$_2$—CH$_2$—CH=CH$_2$ | C$_2$H$_5$ | 130 |
| 47 | Cl | Cl | CH$_3$ | CH$_2$—CH$_2$—CH=CH$_2$ | C$_2$H$_5$ | 140 |
| 48 | Cl | Cl | C$_2$H$_5$ | t-C$_4$H$_9$ | C$_2$H$_5$ | 140 |
| 49 | Cl | Cl | CH$_3$ | —CH$_2$—C$_6$H$_5$ | C$_2$H$_5$ | 180 |
| 50 | Cl | Cl | CH$_3$ |  | H | 167 |
| 51 | CH$_3$ | CH$_3$ | CH$_3$ | | H | 159 |
| 52 | CH$_3$ | CH$_3$ | CH$_3$ | i-C$_3$H$_7$ | H | 185 |
| 53 | Cl | Cl | CH$_3$ | i-C$_3$H$_7$ | H | 188 |
| 54 | CH$_3$ | CH$_3$ | CH$_3$ | i-C$_3$H$_7$ | C$_2$H$_5$ | 145-147 |

FORMULATION EXAMPLES

A: Suspension powder
25% by weight of a compound of formula I
55% by weight of kaolin
10% by weight of colloidal silicic acid
9% by weight of lignin sulfonate
1% by weight of sodium tetrapropylene benzenesulfonate B: Suspension powder
80% by weight of a compound of formula I
8% by weight of calcium lignin sulfonate
5% by weight of colloidal silicic acid
5% by weight of sodium sulfate
2% by weight of sodium diisobutylnaphthalenesulfonate.

HERBICIDAL TEST DATA

The herbicidal activity and compatibility of the compounds of the invention were tested in greenhouse tests and the results were evaluated on a ten-point scale, where 1=100% activity and 10=no activity. Plants I to III were weeds, while IV to VI were useful plants.

| Active substance | Quantity applied in kg/ha | I | II | III | IV | V | VI |
|---|---|---|---|---|---|---|---|
| Example 1 | 1 | 1 | 1 | 1 | 10 | 10 | 10 |
| | 0.5 | 2 | 1 | 1 | 10 | 10 | 10 |
| Table I | 1 | 1 | 1 | 1 | — | 10 | 10 |
| No. 6 | 0.5 | 1 | 1 | 1 | — | 10 | 10 |

I: *Echinocloa crus-galli*
II: *Cynodon dactylon*
III: *Digitaria sanguinalis*
IV: *Oryza sativa*
V: *Gossypium hirsutum*
VI: *Glyzine max.*

As the Table shows, the active compounds of the invention combine a very good activity (predominantly 1 on the assessment scale) with excellent compatibility (10 on the assessment scale in every case) with the useful plants.

Various modifications of the compounds and methods of the invention may be made without departing from the spirit or scope thereof and it is to be understood that the invention is intentended to be limited only as defined in the appended claims.

What we claim is:

1. A compound of the formula

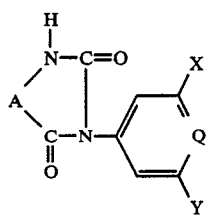

wherein Q is —CH= or —N=;

A is 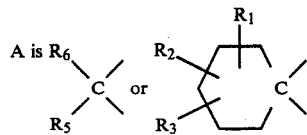

$R_1$, $R_2$ and $R_3$ are each independently hydrogen or alkyl of 1 to 4 carbon atoms, at least one of $R_1$, $R_2$ and $R_3$ being hydrogen; $R_4$ and $R_5$ are each independently alkyl of 1 to 4 carbon atoms or cycloalkyl of 3 to 6 carbon atoms; provided that at least one of them is $C_3$-alkyl or $C_3$-cycloalkyl; and X and Y are halogen, with the proviso that Q is not —CH= when A is

2. A compound of claim 1 wherein X is chlorine or bromine, and Y is chlorine or bromine.

3. The compound of claim 1 which is cyclohexane-5'-spiro-3'-(3,5-dichlorophenyl)-hydantoin.

4. A compound of claim 1, where A is

5. A compound of claim 1, where A is

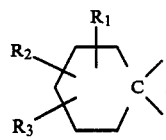

6. The compound of claim 1 which is 5',5'-diisopropyl-3-[4-(2,6-dichloropyridyl)]-hydantoin.

7. An herbicidal composition comprising an herbicidally effective amount of at least one compound of claim 1 and an inert carrier.

8. A composition of claim 7 wherein X is chlorine or bromine, and Y is chlorine or bromine.

9. A composition of claim 7 wherein the active compound is 2-methyl-cyclohexane-5'-spiro-3'-(3,5-dichlorophenyl)-hydantoin.

10. A herbicidal composition of claim 7 wherein the active compound is 5',5'-diisopropyl-3-[4-(2,6-dichloropyridyl)]-hydantoin.

11. The method of selectively combatting weeds and wild grass comprising contacting weeds and wild grass with an herbicidally effective amount of at least one compound of claim 1.

12. The method of claim 11 wherein X is chlorine or bromine, and Y is chlorine or bromine.

13. The method of claim 11 wherein the active compound is 2-methyl-cyclohexane-5'-spiro-3'-(3,5-dichlorophenyl)-hydantoin.

* * * * *